United States Patent [19]

Gleeson

[11] 4,121,976

[45] Oct. 24, 1978

[54] CULTURING BOTTLE AND METHOD OF MAKING

[76] Inventor: Christopher Michael Gleeson, 140 Railway Ave., Ringwood East, Victoria, Australia, 3135

[21] Appl. No.: 696,215

[22] Filed: Jun. 15, 1976

[30] Foreign Application Priority Data

Jun. 20, 1975 [AU] Australia .............................. 2060/75
Aug. 29, 1975 [AU] Australia .............................. 2972/75

[51] Int. Cl.² .............................................. C12B 1/00
[52] U.S. Cl. .................................... 195/104; 195/139; 215/6
[58] Field of Search ............... 195/127, 139, 101, 102, 195/103.5 R, 104; 215/6

[56] References Cited

U.S. PATENT DOCUMENTS

| | | | |
|---|---|---|---|
| 649,864 | 5/1900 | Rodiger | 215/6 |
| 941,278 | 11/1909 | Schmitt | 215/6 |
| 1,060,023 | 4/1913 | Potter | 215/6 |
| 3,449,210 | 6/1969 | Rohde | 195/139 |
| 3,563,859 | 2/1971 | Fink | 195/139 X |
| 3,589,983 | 6/1971 | Holderith et al. | 195/139 |

Primary Examiner—Raymond N. Jones
Assistant Examiner—Robert J. Warden
Attorney, Agent, or Firm—Andrus, Sceales, Starke & Sawall

[57] ABSTRACT

The invention relates to a culture bottle comprising a side wall, a base on which the bottle can stand, and a partition wall within the bottle extending generally vertically when the bottle is standing on the base; and wherein the side wall is capable of supporting the bottle non-rollingly on its side and in which position the partition wall at least in part defines a dish capable of retaining material.

The invention also relates to methods of preparing a bottle for culturing and culturing methods.

28 Claims, 2 Drawing Figures

4,121,976

CULTURING BOTTLE AND METHOD OF MAKING

BACKGROUND OF THE INVENTION

FIELD OF THE INVENTION

This invention relates to culturing and to culture apparatus.

Reference is made to U.S. Pat. Nos. 3,589,983; 2,992,974; 3,073,750; and 3,796,638 which disclose culturing containers and techniques.

SUMMARY OF THE INVENTION

The present invention provides a culture bottle comprising a side wall, a base on which the bottle can stand, and a partition wall within the bottle extending generally vertically when the bottle is standing on the base; and wherein the side wall is capable of supporting the bottle non-rollingly on its side and in which position the partition wall at least in part defines a dish capable of retaining culturing base material.

PREFERRED ASPECTS

The side wall may have a portion inclined to the vertical when the bottle is on its base so that when the bottle is supported on that portion the partition wall forms the aforesaid dish. However, it is preferred that the side wall extends generally vertical and that the partition wall is inclined to the vertical when the bottle is on its base and/or that the partition wall has a lip so as to form the aforesaid dish.

It is preferred that the partition wall has projections thereon which extend upwardly when the bottle is in said position. These projections will assist in holding agar in the dish.

It is preferred that the surface of the side wall above the dish, when the bottle is in said position, is substantially flat.

It is preferred that there is an access opening which provides direct access to both of the compartments defined by the side wall and the partition wall.

It is particularly preferred that the bottle is square or more preferably rectangular when seen in plan when standing on its base as this will assist stacking of bottles side by side for autoclaving as described below.

The partition wall preferably extends from the base.

The bottle may be made of any suitable material but glass and synthetic plastics material are preferred.

It is preferred that the compartment on the dish defining side of the partition wall is smaller than the other compartment.

The above described bottle is particularly useful in culturing and in a preferred method of preparing a bottle for culturing, agar or other culturing base material (of which silica gel is one example) is introduced into the compartment on the dish defining side of the partition wall and nutrient for material to be cultured is introduced into the other compartment. Thereafter the bottle is autoclaved whilst standing on its base, during which the agar or other culturing base material will liquify. The bottle is then placed in said position so that the agar lies in the dish and, after cooling solidifies to form what is known as an agar slope or slant and the nutrient is in the other compartment. The bottle is then ready for culturing and will normally be maintained in sealed sterile condition.

In the preferred method of culturing, a material to be cultured is introduced into the nutrient or onto the agar. Then or previously and, if desired, at intervals during culturing, the bottle is tipped off its base to distribute nutrient and perhaps also material to be cultured over the agar. The material to be cultured is cultured with the bottle either in said position or on its base. Normally the material to be cultured will be incubated and cultured at 37°C. Cultures will grow on the agar and also in the nutrient but will normally only be readily observable on the former.

The above method of culturing has the particular advantages that the nutrient will not significantly obscure observation of cultures growing on the agar — this is particularly important where blood is introduced into the nutrient and which, by its colour and opacity, tends to obscure. Further, material introduced into the nutrient can slow culturing — blood is bacteriocidal and will slow culturing — and this substantial absence of nutrient from the agar is an advantage.

The bottle can also be used for subculturing and for the testing of antibiotics.

Accordingly, the invention also provides culture apparatus comprising a bottle in accordance with this invention containing agar in the compartment on the dish defining side of the partition wall and, preferably, nutrient in the other compartment.

This invention also provides the culture apparatus and in sterile condition and an another instance with blood or other material to be cultured in the nutrient.

Further, this invention also provides a method for culturing comprising displacing nutrient to and from agar on the dish of a bottle in accordance with this invention from and to the other compartment.

A specific construction of a bottle in accordance with this invention will now be described with the aid of the accompanying drawings.

DETAILED DESCRIPTION

Figure 1:
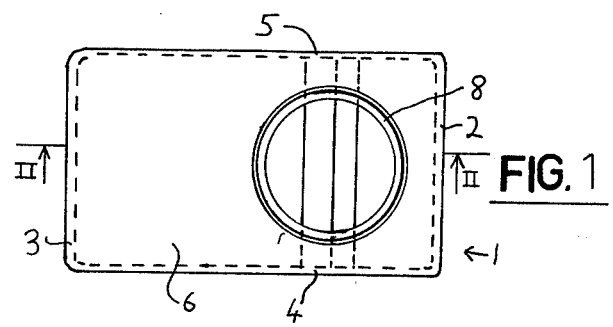
FIG. 1 is a plan view of the bottle.

The bottle 1 shown in the drawings comprises a first, flat, side 2, a second, flat, side 3, a third side 4 which is preferably flat and a fourth side 5 which is also preferably flat. The bottle 1 also has a top surface 6, a base 7, a neck 8 provided with screwthread 9 and an angled lip 11.

In addition, the bottle has a partition wall 12 provided with a lip 13 and projections 14.

The wall 12 divides the bottle into a first compartment 17 and a second compartment 16 of respectively, about ⅔ and ⅓ of the total volume of the bottle.

It will be noted that the neck 8 gives access to both compartments 16 and 17.

In use the bottle is prepared for culturing initially when standing on a horizontal base such as indicated by 18 and say about 30 ml. agar is placed in compartment 16 and about 50-60 ml. of nutrient is placed in compartment 17.

Figure 2:
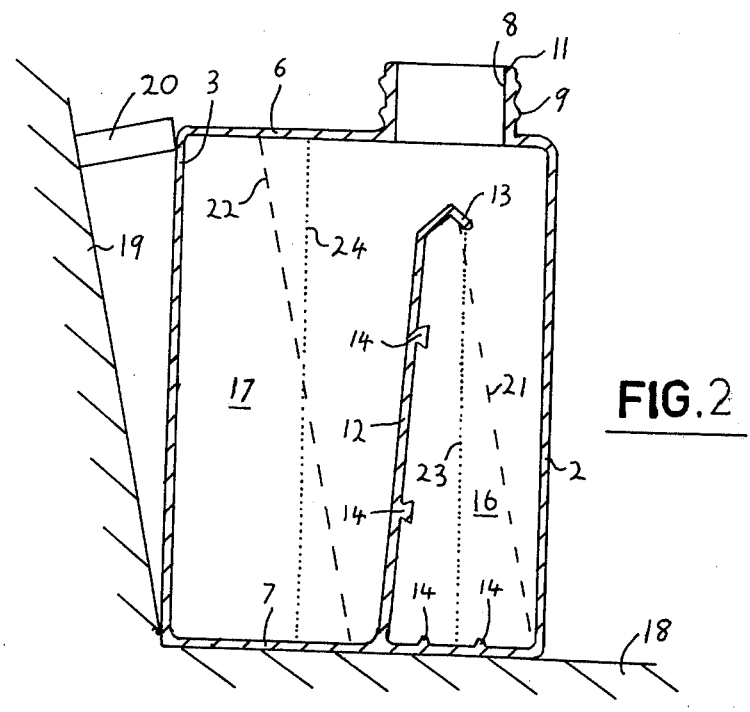
FIG. 2 is a cross-section on line II — II in FIG. 1.

After autoclaving and sealing, the lip 11 assisting in clamping engaging a seal between the neck 8 and a cap (not shown) to hinder sucking into the bottle, the bottle is placed on its side 3 on a horizontal base such as indicated by 19 (with re-orientation of FIG. 2 so that base 19 is horizontal) and supported, as is usual, by a block or other member 20. The agar and nutrient will flow to be as depicted by dash lines 21 and 22. In the event that the member 20 is not in use and the side 3 is stood on a horizontal surface the agar and nutrient will flow to be as depicted by dotted lines 23 and 24. After setting of the agar the bottle is ready for use in culturing.

Culturing can be performed as above and in addition to the advantages above the bottle as shown also has the advantages that side 3 makes a good support and slide 2 being flat allows a good view of the agar.

The above described bottle is preferably made from glass or from synthetic plastics materials. Examples of the latter are polycarbonate and TPX. Manufacture of the bottle shown is preferably by moulding of all but one of walls 4 and 5 and subsequent attachment of that wall.

The nutrients and agar or other base culturing material used can be any materials suitable to the particular material to be cultured.

The bottle of the above described invention is simple to make and is effective. It takes up less space in autoclaves than other bottles known to applicant. It also rattles less in autoclaves, stacks better and is easier to store and transport. It takes up less space when culturing and gives an excellent substantially undistorted viewing. Further, it enables nutrient and culturing base material to be autoclaved together whereafter a bottle is sterilized and prepared ready for use.

Modifications and adaptions may be made to the above described without departing from the spirit and scope of this invention which includes every novel feature and combination of features disclosed herein.

The claims form part of the disclosure of this specification.

I claim:

1. A bottle for growing microbiological cultures comprising:
    a plurality of contiguous side walls each having a pair of edges, one of which is joined to said base, said plurality of side walls extending away from said base to form a container, one of said side walls being formed for supporting the bottle in a stable condition on a surface when the bottle is in a second position, angularly displaced from said first position.
    a cover joined to the other edges of said side walls for completing the closure of the container, said cover having an access opening therein permitting communication with the interior of the container;
    a partition wall means within said bottle joined to said base and extending therefrom, said partition wall means joined to said side walls and spanning the interior of said container and oriented with respect to said one side wall for forming a material retaining dish when said bottle is supported by said one side wall, said partition wall means dividing said bottle into a first compartment on one side thereof for providing material to said dish and a second compartment on the other side thereof when said bottle is supported by said base; and
    culturing base material in at least one of said first compartment or dish.

2. A bottle as claimed in claim 1 further defined as having culturing base material in said dish and presenting a generally horizontal culturing base material surface when said bottle is in said second position.

3. A bottle as claimed in claim 1 further defined as including a nutrient in said second compartment.

4. A bottle as claimed in claim 3 wherein said access opening is so located on said cover so as to permit communication on either side of said partition wall means.

5. A bottle as claimed in claim 4 wherein the length of the said partition wall means is less than that of said side walls and said partition wall means terminates below said access opening.

6. A bottle as claimed in claim 1 wherein said one side wall is generally vertical when said bottle is supported on said base and said partition wall means is inclined to the vertical when the bottle is supported on said base.

7. A bottle as claimed in claim 6 wherein said partition wall means is inclined away from said one side wall in a direction away from said base.

8. A bottle as claimed in claim 1 wherein said side walls comprise four substantially flat side walls joined to one another and to said base and cover at substantially right angles, one of said side walls comprising said one side wall, said partition wall means joined to the side walls adjacent said one side wall.

9. A bottle as claimed in claim 1 wherein said partition wall means has at least one projection extending away from said partition wall means for retaining said culturing base material in said dish.

10. A bottle as claimed in claim 1 wherein said partition wall means has first and second ends and a pair of sides, said first end being joined to said base, said sides being joined to said side walls and said second end forming a lip exposed to the interior of the bottle along substantially all of its dimension.

11. A bottle as claimed in claim 1 wherein said partition wall means is joined to said base at a position therealong such that the volume of said bottle on the side of said partition wall means on which said dish is formed is less than the volume on the other side.

12. A bottle as claimed in claim 11 wherein said partition wall means is joined to said base at a position therealong such that the volume of said bottle on the side of said partition wall means on which said dish is formed is approximately one half of the volume on the other side.

13. A culture bottle comprising:
    a base for supporting said bottle on a surface when said bottle is in a first position;
    a plurality of contiguous side walls each having a pair of edges, one of which is joined to said base, said plurality of side walls extending away from said base to form a container, one of said side walls being formed for supporting the bottle in a stable condition on a surface when the bottle is in a second position, angularly displaced from said first position;
    a cover joined to the other edges of said side walls for completing the closure of the container, said cover having an access opening therein permitting communication with the interior of the container; and
    a partition wall means within said bottle joined to said base and extending therefrom, said partition wall means joined to said side walls and spanning the interior of said container and oriented with respect to said one side wall for forming a material retaining dish when said bottle is supported by said one side wall.

14. A culture bottle as claimed in claim 13 wherein said partition wall means has first and second ends and a pair of sides, said first end being joined to said base, said sides being joined to said side walls and said second end forming a lip exposed to the interior of the bottle along substantially all of its dimension.

15. A culture bottle as claimed in claim 13 wherein said one side wall is generally vertical when said bottle is supported on said base and said partition wall means is inclined to the vertical when the bottle is supported on said base.

16. A culture bottle as claimed in claim 15 wherein said partition wall means is inclined away from said one side wall in a direction away from said base.

17. A culture bottle as claimed in claim 13 wherein said side walls are transparent and a portion of the side wall above said dish when said bottle is in said second position is formed for viewing said dish.

18. A culture bottle as claimed in claim 17 wherein the portion of the side wall above said dish has inside and outside surfaces which are substantially flat for providing an undistorted view of said dish.

19. A culture bottle as claimed in claim 13 wherein said access opening is so located on said cover as to permit communication on either side of said partition wall means.

20. A culture bottle as claimed in claim 19 wherein the length of the said partition wall means is less than that of said side walls and said partition wall means terminates below said access opening.

21. A culture bottle as claimed in claim 13 wherein said side walls comprise four substantially flat side walls joined to one another and to said base and cover at substantially right angles, one of said side walls comprising said one side wall, said partition wall means joined to the side walls adjacent said one side wall.

22. A culture bottle as claimed in claim 21 wherein the height of said side walls exceed their width when said bottle is in said first position.

23. A culture bottle as claimed in claim 13 wherein said partition wall means has at least one projection extending away from said partition wall means to enhance the material retaining properties thereof.

24. A culture bottle as claimed in claim 13 wherein said partition wall means is joined to said base at a position therealong such that the volume of said bottle on the side of said partition wall means on which said dish is formed is less than the volume on the other side.

25. A culture bottle as claimed in claim 24 wherein said partition wall means is joined to said base at a position therealong such that the volume of said bottle on the side of said partition wall means on which said dish is formed is approximately one half of the volume on the other side.

26. A method of preparing a culture bottle, said culture bottle having an internal partition wall means forming first and second side-by-side compartments when said bottle is in a first position and a dish for containing the contents of said first compartment when said bottle is in a second position, said first compartment containing a culturing base material which is solid at culturing temperatures and molten at elevated temperatures, said method comprising the steps of:
placing said bottle in said first position;
heating the bottle with the bottle in said first position to melt the culturing base material;
placing said bottle in said second position to place the culturing base material in the dish formed by said partition wall means; and
cooling the bottle to solidify the culturing base material in the dish.

27. A method as claimed in claim 26 further including the step of introducing the culturing base material into said first compartment and a nutrient into said second compartment prior to heating the bottle.

28. The method according to claim 27 defined as a method for growing a culture and further including the stop of introducing the material to be cultured on at least one of the culturing base material in the dish and the nutrient, and tipping the bottle to flow the nutrient in said second compartment on the solidified culturing base material in the dish.

* * * * *